United States Patent [19]

Venturello et al.

[11] Patent Number: 4,754,073

[45] Date of Patent: Jun. 28, 1988

[54] METHOD FOR THE PREPARATION OF KETONES

[75] Inventors: Carlo Venturello, Novara; Mario Gambaro, Pernate; Marco Ricci, Rome, all of Italy

[73] Assignees: Instituto Guido Donegani S.p.A., Novara; Consiglio Nazionale Delle Ricerche, Rome, both of Italy

[21] Appl. No.: 1,377

[22] Filed: Jan. 8, 1987

[30] Foreign Application Priority Data

Jan. 16, 1986 [IT] Italy ................................ 19098 A/86

[51] Int. Cl.$^4$ ............................................. C07C 45/29
[52] U.S. Cl. .................................... 568/311; 568/385; 568/342
[58] Field of Search ........................ 568/311, 342, 385

[56] References Cited

U.S. PATENT DOCUMENTS

| | | | |
|---|---|---|---|
| 4,171,313 | 10/1979 | Mares et al. | 568/385 |
| 4,480,135 | 10/1984 | Esposito et al. | 568/385 |

FOREIGN PATENT DOCUMENTS

0151941  8/1985  European Pat. Off. ............ 568/385

OTHER PUBLICATIONS

Venturello et al., J. Org. Chem.; vol. 48, pp. 3831–3833 (1983).

Venturello et al., Chem. Abst.; vol. 104, #27804t (1985).
Agrawal et al., Chem. Abst.; vol. 102, #173251k, (1985).
Bortalini et al., Chem. Abst.; vol. 103, #122757t, (1985).
Barry M. Trost and Yoshiro Masuyama, "Molybdenum Catalyzed Reactions Selectivity in Oxidations with Hydrogen Peroxide and Ammonium Molybdate", Israel Journal of Chemistry, vol. 24, 1984, pp. 134–143.
S. E. Jacobson, D. A. Muccigrosso, and F. Mares, "Oxidation of Alcohols by Molybdenum and Tungsten Peroxo Complexes," Journal of Organic Chemistry, vol. 44, No. 6, 1979, pp. 921–924.

*Primary Examiner*—James H. Reamer
*Attorney, Agent, or Firm*—Stiefel, Gross & Kurland

[57] ABSTRACT

Method for the preparation of ketones, by means of oxydation of the corresponding secondary alcohols, characterized in that said alcohols are catalytically oxidized by $H_2O_2$ inside a two-phase system comprising:

(a) an aqueous phase, containing hydrogen peroxide as the oxidizing agent;
(b) an organic phase, containing a secondary alcohol and optionally a solvent immiscible with said aqueous phase, as well as a peroxidic catalyst having the general formula $Q_3XW_4O_{24}$, wherein X represents an atom of phosphorus or of arsenic and wherein Q represents a quaternary cation, containing hydrocarbon groups having a total of from 20 to 70 C atoms.

11 Claims, No Drawings

METHOD FOR THE PREPARATION OF KETONES

BACKGROUND OF THE INVENTION

The oxidation of secondary alcohols to ketones is one of the basic reactions of the organic synthesis; as an example, mentioning the oxidation of isoborneol or of borneol for obtaining camphor will be sufficient. Many known processes are based on the oxidation of the corresponding secondary alcohols; such processes show, however, heavy drawbacks. Some (stoichiometrical) processes require the use of considerable amounts of expensive oxidizing agents, or of agents which create heavy environmental problems for their recovery or disposal at the reaction end; as an example, we may mention, besides $HNO_3$, oxalyl chloride, N-halosuccinimides, and the pentavalent vanadium, hexavalent chromium and heptavalent manganese compounds.

Other (catalytic) processes, although preferable than the first ones, from the environmental point of view, are not completely satisfactory, because of the long reaction time (see, e.g., the $PdCl_2$-/$NaOAc$/$O_2$ system, or the benzyltrimethylammonium tetrabromo-oxomolybdate/tert.butyl hydroperoxide system), or because of the particularly expensive ($PtO_2$ or $RuO_4$), or toxic ($OsO_4$) catalysts used. Among the catalytic methods, examples are known of oxidation with hydrogen peroxide, the use of which could offer, in principle, undoubted advantages, thanks to their limited cost and to the absence of a reduction product to be disposed of. But also these methods show a poor practical interest, in that:

They require extremely long reaction times (from 1 to 7 days) the catalytic activity being very low (Trost: Israel J. Chem. 1984, 24, 134); or It is necessary to work with $H_2O_2$ at 90%, with evident safety problems (Mares: J. Org. Chem., 1973, 44, 921).

The Applicants have now found that it is possible to oxidize secondary alcohols to ketones by means of a simple and cheap process, free from the drawbacks to be faced in case of the known processes, by using low-concentration aqueous $H_2O_2$ resorting to a suitable catalytic system.

DISCLOSURE OF THE INVENTION

In its broadest aspect, the invention consists of a catalytic method for the preparation of ketones having formula (I):

(I)

by means of the oxidation of the corresponding secondary alcohols having formula (II):

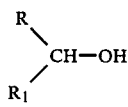
(II)

wherein R and $R_1$, equal to or different from each other, are alkyl or aryl-alkyl groups having up to 20 C atoms, aryl or alkyl-aryl groups having from 6 to 12 C atoms or cycloalkyl groups having from 3 to 12 C atoms; obviously R and $R_1$ can be bound to each other, so as to form an alkylic cycle containing from 5 to 12 C atoms, or a polycyclic system. The process is characterized in that said alcohols (II) are oxidized to the corresponding ketones (I) by reacting them with $H_2O_2$, under stirring at 60°–95° C., inside a biphasic system comprising:

(a) an aqueous phase, containing hydrogen peroxide as the oxidizing agent;

(b) an organic phase, consisting of a secondary alcohol and optionally of a solvent immiscible with said aqueous phase, as well as of a peroxidic catalyst having the general formula $Q_3XW_4O_{24}$ (III), wherein X represents an atom of phosphorus or of arsenic, and wherein Q represents a quaternary cation $(R_2R_3R_4R_5M)^+$, wherein M is selected from nitrogen and phosphorus and wherein $R_2$, $R_3$, $R_4$ and $R_5$, equal to or different from each other, are selected from hydrogen and hydrocarbon groups, so as to have from 1 to 4 hydrocarbon groups containing a total of from 20 to 70 C atoms.

By such a method, the desired ketones are obtained with optimum yields and in a very pure form; an illustrative, but not limitative example of the alcohols which can be oxidized according to the invention is represented by:

hexane-2-ol;
octane-2-ol;
decane-2-ol;
cyclohexanol;
2,6-dimethyl-cyclohexanol;
menthol;
1-phenyl-ethanol;
borneol;
isoborneol;
6-hydroxy-heptanoic acid;
benzhydrol;
2-ethyl-1,3-hexanediol;
dihydrocholesterol;
1,2,3,4,5,6,7,8-octahydro-2-hydroxy-naphthalene.

Oxidation catalyst (III) is consisting of a peroxidic complex, containing tungsten, phosphorus (or As), and a sufficiently lipophilic quaternary cation, that can be obtained according to usual techniques.

According to a preferred but not limitative form, it is better to use, as a catalyst, a compound having formula (III), wherein X represents phosphorus, wherein M (in the quaternary cation Q) represents nitrogen and wherein $R_2$, $R_3$, $R_4$, $R_5$ are hydrocarbon groups containing a total of from 25 to 40 C atoms, such as, e.g., methyltrioctylammonium, dimethyldihexadecylammonium, dimethyldioctadecylammonium, or mixtures thereof; in particular, as the catalysts, the compounds having formula:

$$(C_{25}H_{54}N)_3PW_4O_{24} \quad (IV)$$

and $$(C_{37}H_{78}N)_3PW_4O_{24} \quad (V)$$

are preferred.

The catalysts having formula (IV) and (V) can be prepared, e.g., by reacting tungstic acid (or an alkali-metal tungstate), phosphoric acid (or an alkali-metal phosphate) and hydrogen peroxide, inside an acidic aqueous phase, with a quaternary salt, selected from the group consisting of methyltrioctylammonium chloride (known on the market under the trade name ALIQUAT 336) and dimethyl [dioctadecyl (75%)+dihexadecyl (25%)]ammonium chloride (known on the market under the trade name ARQUAD 2HT), contained in an organic phase immiscible with the aqueous phase. The reaction between the inorganic reactants can be carried out at from 20° to 80° C.; then the quaternary salt dissolved in a solvent (preferably in 1,2-dichloroethane) is added, preferably at room temperature, and stirring of the biphasic mixture is continued for 15–30 minutes. The acidic aqueous phase was preferably a pH lower than 2; for the purpose of obtaining such a range of values, pH is adjusted, if necessary, with a mineral acid (e.g., $H_2SO_4$ or HCl). In general, the molar ratios between the reactants must be the following: per each mol of P, 4 mol of W and up to 2 mol of quaternary salt; as to $H_2O_2$, from 2.5 to 6 mol of $H_2O_2$ per mol of W are enough. After the separation of the phases, by evaporation of the organic phase, the compound (IV) or the compound (V) is obtained, respectively, in the oil or in the solid form. The oxidation reaction is carried out according to the double-phase technique, and the organic phase contains the alcohol, the catalyst, and, optionally, a solvent immiscible with the aqueous phase; said immiscible solvent can be chlorinated hydrocarbons (e.g., 1,2-dichloroethane, trichloroethanes, tetrachloroethylene) or optionally substituted aromatic hydrocarbons (e.g., benzene, toluene or xylenes). Usually, the reaction can be carried out under vigorous stirring, at temperatures from 60° to 95° C. and under atmospheric pressure, which does not exclude, obviously, that the reaction may be carried out under a superatmospheric pressure. The reaction time (according to the used catalyst and to its amount, to the operating temperature, to the nature and to the concentration of the alcohol in the organic phase) is generally from 10 minutes to 2 hours; the catalyst is preferably used in a $H_2O_2$:catalyst molar ratio from 200:1 to 300:1. It is finally recommended to work with an $H_2O_2$:alcohol molar ratio from 1:1 to 2:1, and preferably from 1.2:1 to 1.5:1. When a suitable solvent is used, the alcohol concentration in the organic phase is preferably higher than 70% by weight. The concentration of $H_2O_2$, in the aqueous phase, is not critical, and can be from 1 to 70%, and preferably from 10 to 40% by weight. At the reaction end, after the separation of the phases, the ketone (present in the organic phase) is isolated by distillation or by column chromatography, according to usual techniques. The method of the invention can be performed by means of usual equipment and techniques; the catalyst is sufficiently stable and can be therefore prepared and stored until its use. The invention is now disclosed in greater detail in the following Examples, given for purely illustrative and non-limitative purposes. The concentration of hydrogen peroxide and of phosphoric acid is expressed in the Examples as grams per 100 cm$^3$ of solution.

EXAMPLE 1

Part A

Preparation of catalyst $(C_{25}H_{54}N)_3PW_4O_{24}$ (IV)

To a 4-neck 100-cm$^3$ flask, equipped with blade stirrer and dropping funnel, 3.30 g of $Na_2WO_4.2H_2O$, dissolved in 20 cm$^3$ of $H_2O$, 1.5 cm$^3$ of 40% $H_3PO_4$ and 3 cm$^3$ of $H_2SO_4$ at 30% by weight were charged at room temperature. Two cm$^3$ of 40% $H_2O_2$ were then added. Forty cm$^3$ of 1,2-dichloroethane, containing 1.6 g of methyltrioctylammoniumchloride (known in the trade as ALIQUAT 336), were then added, under vigorous stirring, over a 3-minute time. The stirring was maintained for 20 minutes at room temperature, and at the end reaction mixture was decanted and the phases were separated. The organic (lower) phase was evaporated in vacuo, thus obtaining 2.82 g of a viscous oil. The analytical results are in agreement with the indicated formula, as shown hereinbelow:

Active oxygen found=5.67% (determined by means of the addition of a known excess of $Na_2SO_3$ in a basic medium, and iodometric back-titration in acidic medium).

Theoretical active oxygen=5.68% (computed for 8 active oxygen atoms).

Part B

Oxidation of 2-octanol

To a 2-neck 50-cm$^3$ flask, provided with magnetic stirrer, thermometer and reflux condenser, 6.4 cm$^3$ of 40% $H_2O_2$ (about 75 mmol), 0.56 g (about 0.25 mmol) of catalyst (IV), and 6.5 g (50 mmol) of 2-octanol were charged. The biphasic mixture was heated under vigorous stirring, at 90° C. and was kept at this temperature for 1.5 hours. A conversion of $H_2O_2>98\%$ was obtained (as determined by iodometric titration of the aqueous phase). At the end, the phases were separated. The aqueous phase was extracted with ethyl ether and the extract was added to the organic phase. The solvent was evaporated off and the residue was eluted over a silica gel column, using an ether/n-hexane (1:1) mixture as the eluent. 5.9 g (46.1 mmol) of 2-octanone were obtained with a purity>99%, as determined by gas-liquid chromatography (GLC). The yield, with respect to the used alcohol, was 92%.

EXAMPLE 2

Example 1 was repeated, replacing 2-octanol by 1-phenylethanol (6.1 g; 50 mmol), and reducing the reaction time to 10 minutes; 5.4 g (45 mmol) of acetophenone were obtained (GLC purity: 98%), which corresponds to a 90% yield.

EXAMPLE 3

Example 1 was repeated, replacing 2-octanol by (−)-menthol (7.8 g; 50 mmol), increasing the reaction time to 2 hours, and eluting the residue of the organic phase over a column of alumina (instead of silica); 6.78 g (44 mmol) of (−)-menthone were obtained (GLC purity>99%), which corresponds to a 88% yield.

EXAMPLE 4

Example 1 was repeated, replacing 2-octanol by 2-ethyl-1,3-hexanediol (7.3 g; 50 mmol) and reducing the reaction time to 1 hour; 5.48 g (38.1 mmol) of 3-hydroxymethyl-4-heptanone were obtained (GLC purity>99%), which corresponds to a yield of 76%.

EXAMPLE 5

Example 1 was repeated, replacing 2-octanol by (±)-isoborneol (7.7 g; 50 mmol), adding 2 cm$^3$ of tetrachloroethylene and reducing the reaction time to 45 minutes. 7.22 g (47.5 mmol) of (±)-camphor were obtained (GLC purity>99%), which corresponds to a 95% yield.

EXAMPLE 6

Example 3 was repeated, replacing (−)-menthol by 2,6-dimethylcyclohexanol (6.4 g; 50 mmol), using 5.1 cm³ (60 mmol) of 40% of $H_2O_2$, adding 4 g of anhydrous $MgSO_4$ and reducing the reaction time to 30 minutes. 5.61 g (44.5 mmol) of 2,6-dimethyl-cyclohexanone were obtained (GLC purity>99%), which corresponds to a 89% yield.

EXAMPLE 7

Part A

Preparation of catalyst $(C_{37}H_{78}N)_3PW_4O_{24}$ (V)

By operating as described in Example 1, but replacing ALIQUAT 336 with 3.10 g of dimethyl[dioctadecyl (75%)+dihexadecyl (25%)]ammonium chloride (known in the trade as ARQUAD 2HT), 3.6 g of a white solid were obtained. The analytical values are in agreement with the indicated formula, Active oxygen found=4.60% (determined as in Example 1);

Theoretical active oxygen=4.63% (computed for 8 active oxygen atoms).

Part B

Oxidation of benzhydrol

Example 3 was repeated, replacing catalyst (IV) to 0.69 g (0.25 mmol), of catalyst (V), replacing 2-octanol with 9.20 g (50 mmol) of benzhydrol, and reducing the reaction time to 1 hour. 9.04 g (49.7 mmol) of benzophenone were thus obtained (GCL purity>99%), which corresponds to a 99% yield.

EXAMPLE 8

Example 5 was repeated, replacing (±)-isoborneol by (−)-borneol (7.7 g; 50 mmol); 6.99 g (46 mmol) of (−)-camphor were obtained (GLC purity 97.8%), which corresponds to a 92% yield.

EXAMPLE 9

To a 2-neck 50-cm³ flask, provided with magnetic stirrer, termomether and reflux condenser, 3.2 cm³ of 40% $H_2O_2$ (37.6 mmol), 10 cm³ of tetrachloroethylene, 0.28 g (about 0.125 mmol) of catalyst (IV), and 9.9 g of 90% dihydrocholesterol (25 mmol) were charged. The biphasic mixture was heated at 90° C. under vigorous stirring and was kept at this temperature for 45 minutes. A conversion of $H_2O_2$>98% was obtained (as determined by iodometric titration of the aqueous phase). At the end, the phases were separated. The solvent of the organic phase was evaporated off and the residue was eluted over a silica gel column, using methylene chloride as the eluent. 8.80 g (22.8 mmol) were obtained of cholestan-3-one (melting point: 129°–130° C., after crystallization from ethanol). The yield, with respect to the used alcohol, was 91%. Data and results of all of the tests are reported in the following table:

TABLE 1

| Example | Alcohol (50 mmol)(*) | Catalyst (0.25 mmol) | Solvent | Time | T (°C.) | Yield (%) |
|---|---|---|---|---|---|---|
| 1 | Octanol | IV | — | 1.5 hrs | 90 | 92 |
| 2 | 1-Phenylethanol | IV | — | 10 min. | 90 | 90 |
| 3 | (−)-Menthol | IV | — | 2.0 hrs | 90 | 88 |
| 4 | 2-Ethyl-1,3-hexanediol | IV | — | 1.0 hrs | 90 | 76 |
| 5 | (±)-Isoborneol | IV | $C_2Cl_4$ | 45 min. | 90 | 95 |
| 6 | Dimethyl-cyclohexanol(**) | IV | — | 30 min. | 90 | 89 |
| 7 | Benzhydrol | V | — | 1 hr | 90 | 99 |
| 8 | (−)-Borneol | IV | $C_2Cl_4$ | 45 min. | 90 | 92 |
| 9 | Dihydrocholesterol | IV | $C_2Cl_4$ | 45 min. | 90 | 91 |

(*)$H_2O_2$ at 40% (about 75 mmol), but for Example 6:
(**)Addition of anhydrous $MgSO_4$ (4 g); 40% $H_2O_2$: 60 mmol.

What we claim is:

1. A catalytic method for the preparation of a ketone having formula (I):

by means of oxidation of the corresponding secondary alcohol having formula (II):

wherein R and $R_1$ are equal to or different from each other, and are selected from the group consisting of alkyl or aryl-alkyl groups of from 6 to 12 carbon atoms, aryl or alkyl-aryl groups having up to 20 carbon atoms and cycloalkyl groups having from 3 to 12 carbon atoms, and wherein R and $R_1$ can be bound to each other to form an alkylic cycle containing from 5 to 12 carbon atoms, or a polycyclic system, characterized in that said alcohol is oxidized in a liquid system comprising:

(a) an aqueous phase, containing, as an oxidizing agent, hydrogen peroxides; and (b) an organic phase, containing a secondary alcohol and a peroxidic catalyst having the general formula $Q_3XW_4O_{24}$ (III), wherein X represents an atom of phosphorus or of arsenic, Q represents a quaternary cation $(R_2R_3R_4R_5M)^+$, wherein M is selected from the group consisting of nitrogen and phosphorus, and wherein $R_2$, $R_3$, $R_4$ and $R_5$, are equal to or different from each other, and are selected from the group consisting of hydrogen and hydrocarbon groups, so as to have from 1 to 4 hydrocarbon groups containing a total of from 20 to 70 carbon atoms.

2. A method according to claim 1, wherein the catalyst (III) is slected from the group consisting of the compounds of formula:

$(C_{25}H_{54}N)_3 P WO_4O_{24}$, and $(C_{37}H_{78}N)_3 P W_4O_{24}$.

3. A method according to claim 1, characterized in that in catalyst (III), X represents phosphorus, that in the quaternary cation M represents nitrogen, and that the radicals $R_2$, $R_3$, $R_4$ and $R_5$ are hydrocarbon groups containing a total of from 25 to 40 C atoms.

4. A method according to claim 3, wherein the quaternary cation is selected from the group consisting of methyltrioctylammonium, dimethyldioctadecylammonium and dimethyl- or dihexadecylammonium and mixtures thereof.

5. A method according to claim 1, wherein the alcohol is selected from the group consisting of octan-2-ol, 1-phenyl-ethanol, (−)-menthol, 2-ethyl-1,3-hexanediol, (−)-borneol, isoborneol, 2,6-dimethylcyclohexanol, benzhydrol, cyclohexanol, dihydrocholesterol and 1,2,3,4,5,6,7,8-octahydro-2-hydroxy-naphthalene.

6. A method according to claim 1, wherein the oxidation temperature is from 60° to 95° C., the $H_2O_2$:alcohol molar ratio is from 1:1 to 2:1 and the $H_2O_2$:catalyst molar ratio is from 200:1 to 300:1.

7. A method according to claim 1, wherein the concentration of $H_2O_2$ in the aqueous phase is from 1 to 70% by weight.

8. A method according to claim 7, wherein said hydrogen peroxide concentration is from 10 to 40% by weight.

9. A method according to claim 1, wherein said organic phase further comprises a water immiscible solvent.

10. A method according to claim 9, wherein said water immiscible solvent is selected from the group consisting of chlorinated aliphatic hydrocarbons and aromatic hydrocarbons.

11. A method according to claim 10, wherein said aromatic hydrocarbon is substituted.

* * * * *

UNITED STATES PATENT AND TRADEMARK OFFICE
CERTIFICATE OF CORRECTION

PATENT NO. : 4,754,073  Page 1 of 2

DATED : June 28, 1988

INVENTOR(S) : Carlo Venturello et al.

It is certified that error appears in the above-identified patent and that said Letters Patent is hereby corrected as shown below:

Column 5, line 32: Change "GCL" to --GLC--
ABSTRACT, line 3: Change "oxydation" to --oxidation--
Column 1, line 7: Change "as an" to --for--
Column 1, line 8: Delete "mentioning"
Column 1, line 9: Change "will be sufficient" to --may be mentioned--

Column 1, line 20: Change "than" to --to--
Column 1, line 27: After "Among" delete "the"
Column 1, line 30: Delete the comma (,) after "advantages"; same line: change "their" to --its--

Column 1, line 32: Change "snow a poor" to --are of little--
Column 1, line 36: Change "24" to --$\underline{24}$--
Column 1, line 38: Change "44" to --$\underline{44}$--
Column 1, line 43: Delete "case of"
Column 1, line 44: Change "resorting to" to --by using--
Column 1, line 65: After "R$_1$" delete the comma (,) and insert --are--; same line: after "other," insert --and--

Column 2, line 16: After "R$_5$" delete the comma (,) and insert --are--

Column 2, line 17: After "other," insert --and--
Column 2, line 40: Change "is consisting" to --consists--
Column 3, line 10: Change "was" to --has--
Column 3, line 31: After "under" delete "a"
Column 3, line 32: Before "according" insert --which depends--
Column 4, line 1: Change "time" to --period--

UNITED STATES PATENT AND TRADEMARK OFFICE
CERTIFICATE OF CORRECTION

PATENT NO. : 4,754,073

DATED : June 28, 1988

INVENTOR(S) : Carlo Venturello et al.

It is certified that error appears in the above-identified patent and that said Letters Patent is hereby corrected as shown below:

Column 5, line 28: Change "to" to --by--

Column 5, line 43: Change "termometer" to --thermometer--

Column 6, line 36: Change "of from 6 to 12 carbon atoms" to --having up to 20 carbon atoms--

Column 6, line 37: Change "having up to 20 carbon atoms" to --or from 6 to 12 carbon atoms--

Column 6, line 39: After "3 to 12 carbon atoms" change the comma (,) to a semicolon (;)

Column 6, line 44: Change "peroxides" to --peroxide--

Column 6, line 58: Change "slected" to --selected--

Signed and Sealed this

Fifteenth Day of October, 1991

Attest:

HARRY F. MANBECK, JR.

Attesting Officer

Commissioner of Patents and Trademarks